US008663719B2

(12) United States Patent
Patil

(10) Patent No.: US 8,663,719 B2
(45) **Date of Patent: *Mar. 4, 2014**

(54) HERBAL CALF STARTER COMPOSITIONS

(76) Inventor: Prashant Neminath Patil, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/511,355

(22) PCT Filed: Nov. 4, 2010

(86) PCT No.: PCT/IN2010/000726

§ 371 (c)(1), (2), (4) Date: May 22, 2012

(87) PCT Pub. No.: WO2011/061756

PCT Pub. Date: May 26, 2011

(65) Prior Publication Data

US 2012/0288578 A1 Nov. 15, 2012

(30) Foreign Application Priority Data

Nov. 23, 2009 (IN) ........................ 2465/MUM/2009

(51) Int. Cl.
*A61K 36/76* (2006.01)

(52) U.S. Cl.
USPC ........................................................ 424/771

(58) Field of Classification Search
None
See application file for complete search history.

(56) References Cited

U.S. PATENT DOCUMENTS

| | | | | |
|---|---|---|---|---|
| 4,642,317 | A | 2/1987 | Palmquist et al. | 514/558 |
| 6,080,401 | A * | 6/2000 | Reddy et al. | 424/93.3 |
| 2012/0237622 | A1 | 9/2012 | Patil | |
| 2012/0263697 | A1 | 10/2012 | Patil | |
| 2012/0263811 | A1 | 10/2012 | Patil | |

FOREIGN PATENT DOCUMENTS

| | | | | |
|---|---|---|---|---|
| DE | 202006000487 | | 4/2006 | |
| DE | 102006042149 | | 5/2007 | |
| KR | 20030044731 | * | 6/2003 | |
| KR | 20090097727 | | 9/2009 | |
| WO | WO 00/74696 A1 | * | 12/2000 | A61K 35/78 |
| WO | 2002003813 | | 1/2002 | |
| WO | WO 02/26261 A1 | * | 4/2002 | A61K 47/00 |
| WO | 2004052122 | | 6/2004 | |

OTHER PUBLICATIONS

Meeske, R. et al., “The effect of concentrate supplementation on the productivity of grazing Jersey cows on a pasture based system.” In: South African Journal of Animal Science, vol. 36/22006. pp. 105, 110, 2006.

Castillo, A.R. et al., “Effects of feeding rations with genetically modified whole-cottonseed to lactating Holstein cows.” In: Journal of Diary. Science, vol. 87/6, 2004. pp. 1778-1785.

PCT Search Report for PCT/IN09/000571, Jun. 18, 2010.

PCT Search Report for PCT/IN10/000725, Apr. 21, 2011.

PCT Search Report for PCT/IN09/000572, Jun. 14, 2010.

PCT Search Report for PCT/IN10/000726, Apr. 21, 2011.

* cited by examiner

*Primary Examiner* — Suzanne M Noakes
*Assistant Examiner* — Stephen Chong
(74) *Attorney, Agent, or Firm* — C. Rachal Winger; K&L Gates, LLP

(57) ABSTRACT

The present invention relates generally to herbal calf starter compositions for feeding animals, particularly young animals, and methods of making them, and more particularly relates to shelf-stable and cheaper herbal calf starter compositions for overall development of calves to early complete functional maturity and also prevents any infection by acting as immunobooster. The herbal calf starter compositions comprise effective amount of a mixture of herbal extract and/or at least one bioactive fraction from medicinal herbs and one or more additives selected from Energy Source, Protein Source, Carbohydrate source, Chelated/organic Mineral Mixture, Vitamins, Salt, Toxin destroyer and Biocide. The invention also relates to processes for the preparation of such extracts and herbal calf starter compositions.

20 Claims, No Drawings

HERBAL CALF STARTER COMPOSITIONS

CROSS-REFERENCE TO RELATED APPLICATIONS

This application is a U.S. national stage entry of PCT/IN2010/000726 filed Nov. 4, 2010 which claims priority to Indian Application No. 2465/MUM/2009 filed Nov. 23,2009, each of which is incorporated by reference in its entirety herein.

FIELD OF THE INVENTION

The present invention relates generally to herbal calf starter compositions for feeding young calves and its method of making and feeding, and more particularly relates to shelf-stable and cheaper herbal calf starter compositions for proper growth and development of the rumen to achieve overall structural growth and weight gain along with addressing the problems of gynecological disorders which are associated with the calf for complete functional maturity at the desired period.

BACKGROUND OF THE INVENTION

Laying the groundwork is an important part of any successful project. For growing young calves, the groundwork involves proper growth and development of the rumen and no other feedstuff plays a larger role in rumen development than calf starter. Proper rumen development is necessary for performance later in life, but before rumen development can occur, calves must be encouraged to eat calf starter. Calf starter is a crucial link to proper ruminal development and successful weaning. Since intake of dry feed initiates rumen development and allows early weaning, the availability and intake of calf starters is important to calves prior to weaning.

Ruminants, such as cattle, have a four compartment stomach, as opposed to the single stomach that human beings have. Two of these stomach compartments are the abomasum and the rumen. In a mature ruminant, fermentation of feed in the rumen provides the majority of energy and protein to the ruminant. On the other hand, in a newborn ruminant, the rumen is substantially undeveloped and the abomasum is the primary stomach compartment for digestion and nutrient assimilation. Consequently, young ruminants are typically fed a liquid diet containing readily digestible nutrients, since the abomasum is incapable of digesting sufficient amounts of more complex nutrients that typically form the majority of the nutrition found in solid feeds.

A calf is born with a small, underdeveloped, sterile rumen. Rumen development in young calves generally occurs during the first four to eight weeks of life. The consumption of calf starter by young calves at an early age is important for the development of a functioning rumen and to achieve optimal growth. By the fourth week of life, calves should be consuming more nutrients from calf starter than from milk replacer, which increases the importance of feeding a nutritious, highly palatable starter. Calf starters are an important part of every dairy farm's replacement heifer rearing program. Important characteristics when choosing a calf starter include ingredient choice and quality of manufacturing. Other significant qualities of a calf starter include knowing that the calf starter will remain fresh and not develop fines or molds over time.

Cattles are commonly bred and raised to produce food products, such as milk and beef, for human consumption. Maturation of cattle, as evidenced by weight gain, is an important factor that helps determine when a cow is ready to produce milk or is ready for market. Dairy farmers and cattle ranchers are greatly interested in techniques for economically achieving enhanced rates of ruminant weight gain, since such techniques beneficially reduce milk and beef production costs.

There are some patents of interest available for the development of feed compositions/supplements for the young live stock; the relevant ones include U.S. Pat. No. 3,619,200 which discloses the feed or feed supplement for use in increasing the efficiency of protein production relative to feed intake in ruminants wherein a proteinaceous feed material of plant, animal or synthetic origin is rendered resistant to breakdown within the rumen by chemical modification of the protein and/or the application of a protective coating. The U.S. Pat. No. 5,789,001 discloses a ruminally inert fat for a ruminant feed which is made by applying reducing sugars to oilseed meats and heating to induce non-enzymatic browning. The process is controlled to ensure penetration of the reducing sugars into the interior of cracked oilseed meat prior to browning. The browning reaction renders the protein which surrounds the oil resistant to rumen bacterial degradation to thereby encapsulate the oil in a protective matrix. U.S. Pat. No. 7,160,552 discloses a method of feeding ruminants, the method includes feeding a ruminant a fluid animal feed during a feeding period, the fluid animal feed including an animal feed component and the ruminant consuming greater than about 1.25 pounds of the animal feed component per day, based on the dry weight of the animal feed component, during the feeding period; and the method further includes feeding the ruminant a psyllium composition during the feeding period. The invention disclosed in U.S. Pat. Appln. No. 20030194424 relates to a feed for neonates which composed of 94 to 88% of dry matter, 20 to 30% of protein, 6 to 10% of fat, 3 to 6% of fiber, 5 to 7% of ashes, 1.2 to 1.4% of Ca and 0.8 to 1.2 of P. The product's digestibility reaches 93% providing metabolizable energy of 4,200 calories. U.S. Pat. Appln. No. 20070298142 discloses both the liquid and dry form *Morinda citrifolia* enhanced animal food products they contain pasteurized fruit puree and other *M. citifolia* plant products. U.S. Pat. Appln. No. 20080193587 discloses the composition and method for feeding a young livestock animal. The method for producing a composition formulated for young livestock and includes mixing distillers solubles with at least one of a milk replacer powder, whole milk, and waste milk.

The existing calf starter compositions achieve only the rumen development and weight gain for calf but none of them address the problems of gynecological disorders which are associated with the calf for complete functional maturity at the desired period. Hence the prior art compositions therefore leave significant room for improvement of these compositions with natural components as alternatives.

The herbal revolution and its implementation to daily nutrient intake or function food/dietary supplements with desired therapeutic efficacy led the world populations graeat interest in the herbal compositions. This ultimately led to researchers to develop them in functional food and nutraceuticals and finally to develop marketable products. Functional foods are substances that provide health benefits beyond the normal nutritional values and nutrients added, which are not naturally occurring in that food is called as functional fortified food. The plants are the major source among the Indian masses, since most important foods of mankind as these are not only nutritive but are also sometimes indispensable for the maintenance of health.

It would be desirable to more widely employ natural agents such as herbal mixtures in order to benefit from their safe and beneficial activity. In particular, it would be desirable to use natural agents to induce a more rapid response from herbal medicines by stimulating their beneficial action. The desirability of a combination of natural agents would be dependent, however, upon the continued absence of adverse side effects.

There is no availability of the herbal calf starter composition, which contain medicinal herbs and which addresses the problems of proper growth and development of the rumen to achieve overall structural growth and weight gain along with addressing the problems of gynecological disorders which are associated with the calf for complete functional maturity at the desired period. Hence the present inventor aim is to address the above problems without undesired side effects by developing the herbal calf starter compositions mainly comprising medicinal herbs and one or more additives selected from protein and fat sources, chelated minerals and mineral mixture which are used in functional foods, and vitamins.

To achieve the foregoing and other objects and in accordance with the purpose of the present invention, as embodied and broadly described herein, the compositions and process of preparation thereof.

OBJECTS OF THE INVENTION

It is a primary object of the present invention to provide herbal calf starter compositions as aforesaid which are highly effective in addressing the problems of gynecological disorders which are associated with the calf for complete functional maturity at the desired period.

Another object of the invention is to provide novel herbal calf starter compositions for proper growth and development of the rumen to achieve overall structural growth and weight gain.

A further object of the invention is to provide herbal calf starter compositions as aforesaid, which do not produce any undesirable byproducts, which do not cause any side effects to the calf.

A further object of the invention is to provide herbal calf starter compositions as aforesaid, which are safe and practical to use with little technical expertise.

It is a further object of the present invention to provide herbal calf starter compositions having a long shelf life.

STATEMENT OF THE INVENTION

Herbal calf starter compositions comprising effective amount of an mixture of herbal extract and/or at least one bioactive fraction from medicinal herbs and one or more additives selected from Energy Source, Protein Source, Carbohydrate Source, Chelated/organic Mineral Mixture, Vitamins, Salt, Toxin destroyer and Biocide. The mixture of herbal extract comprising medicinal herbs selected from *Emblica officinalis, Tinospora cordifolia, Embelia basaal, Cyprus rotundus, Asparagus racemosus* and *Lepidium sativam*. The effective amount of an extract or bioactive fraction ranges 10 to 30% (w/w) *Emblica officinalis* preferably 20% (w/w), 15 to 40% (w/w) *Tinospora cordifolia* preferably 25% (w/w), 5 to 20% (w/w) *Embelia basaal* preferably /10% (w/w), 5 to 25% (w/w) *Cyprus rotundus* preferably 15% (w/w), 10 to 30% (w/w) *Asparagus racemosus* preferably 20% (w/w) and 5 to 20% (w/w) *Lepidium sativam* preferably 10% (w/w). The effective amount is 1 to 10% (w/w) herbal mixture, 35 to 75% (w/w) Energy Source, 15 to 50% (w/w) Protein Source, 10 to 40% (w/w) Carbohydrate Source, 2% (w/w) Chelated/organic Mineral Mixture, 1% (w/w) Salt, 0.1% (w/w) Vitamins, 0.1% (w/w) Toxin Destroyer, 0.03% (w/w) Biocide. The effective amount is preferably 3% (w/w) herbal mixture, 48.5% (w/w) Energy Source, 25% (w/w) Protein Source, 20% (w/w) Carbohydrate Source, 2% (w/w) Chelated/organic Mineral Mixture, 1% (w/w) Salt, 0.1% (w/w) Vitamins, 0.1% (w/w) Toxin Destroyer, 0.03% (w/w) Biocide. The Energy Source is 20-50% (w/w) maize grind preferably 30% (w/w), 10-30% (w/w) wheat bran fine preferably 15% (w/w), 1-2% (w/w) bypass fat preferably 1.5% (w/w) and 2-8% (w/w) ground nut extract preferably 5% (w/w)._The Protein Source is 10-30% (w/w) soya flour preferably 20% (w/w) and 3-6% (w/w) maize gluten preferably 5.8% (w/w). The Carbohydrate source selected is 10 to 40% (w/w) deoiled rice bran (DORB) preferably 20% (w/w). The process for preparation of herbal calf starter composition comprising:

a) Obtaining the part of medicinal herb from a group comprising leaves, bark, root and aerial parts;
b) drying the plant part of step (a);
c) powdering the dried plant material of step (b) to a coarse powder;
d)mixing the effective amount by weight of powdered or the concentrated extract of medicinal herb to obtain the herbal mixture;
e) the above herbal mixture is added with one or more ingredients selected from Energy Source, Protein Source, Carbohydrate Source, Chelated/organic Mineral Mixture, Vitamins, Salt, Toxin destroyer and Biocide to obtain the herbal calf starter composition.

DESCRIPTION OF THE INVENTION

The present invention relates generally to herbal calf starter compositions for feeding young calves and its method of making and feeding, and more particularly relates to shelf-stable and cheaper herbal calf starter compositions for proper growth and development of the rumen to achieve overall structural growth and weight gain and also for addressing the problems of gynecological disorders which are associated with the calf for complete functional maturity at the desired period. The herbal calf starter compositions comprises an effective amount of an extract and/or at least one bioactive fraction or powder from herbs such as *Emblica officinalis, Tinospora cordifolia, Embelia basaal,Cyprus rotundas, Asparagus racemosus*, and *Lepidium sativam* etc.; and one or more additives of selected from one or more additives selected from Energy Source, Protein Source, Carbohydrate Source, Chelated/organic Mineral Mixture, Vitamins, Salt, Toxin destroyer and Biocide; and process for the preparation of such extracts and herbal calf starter compositions.

By feeding the calf the herbal calf starter composition, that makes the proper growth and development of the calf rumen. This invention provides a unique approach to make herbal calf starter compositions that serves not only for the proper growth and development of the rumen to achieve overall structural growth and weight gain and also addresses the problems of gynecological disorders which are associated with the calf for complete functional maturity at the desired period.

The invention is herbal calf starter formulation of an effective amount of an extract and/or at least one bioactive fraction or powder from medicinal herbs such is *Emblica officinalis, Tinospora cordifolia, Embelia basaal, Cyprus rotundus, Asparagus racemosus*, and *Lepidium sativam* etc.; and one or more additives selected from one or more additives selected from Energy Source, Protein Source, Carbohydrate Source, Chelated/organic Mineral Mixture, Vitamins, Salt, Toxin destroyer and Biocide. By properly adjusting a particular component in the herbal calf starter composition, that results into proper growth and development of the rumen of calf to achieve overall structural growth and weight gain.

The synergistic action of the medicinal herbs along with other ingredients such as one or more additives selected from Energy Source, Protein Source, Carbohydrate Source, Chelated/organic Mineral Mixture, Vitamins, Salt, Toxin destroyer and Biocide makes the calf to proper growth and development of the rumen to achieve overall structural growth and weight gain and which in turn makes the calf to reach complete functional maturity at the desired period.

The herbal calf starter compositions can be used in several forms: powdered feed form, concentrate form, blender form and base mix form.

The compositions of herbal calf starter mainly comprise the following ingredients in the proportion as mentioned below:

| | |
|---|---|
| 1. Herbal Mixture | 1-10% (w/w) of total composition; |
| 2. Energy Source | 35-75% (w/w) of total composition; |
| 3. Protein Source | 15-50% (w/w) of total composition; |
| 4. Carbohydrate Source | 10-40% (w/w) of total composition; |
| 5. Chelated/organic Mineral Mixture | 2% (w/w) of total composition; |
| 6. Salt | 1% (w/w) of total composition; |
| 7. Vitamins | 0.1% (w/w) of total composition; |
| 8. Toxin Destroyer | 0.1% (w/w) of total composition; |
| 9. Biocide | 0.03% (w/w) of total composition. |

1. Herbal Mixture: The medicinal herbs which comprise the core of the herbal calf starter compositions are selected from the following group:

1.1 *Emblica officinalis*: Family-Euphorbiaceae

The bark of Amla is gray in color and peals in irregular patches. Its feathery leaves, which smell like lemon, are of linear oblong shape and size 10 to 12 mm length and 3 to 6 mm width. Its flowers are monoecioius having greenish yellow color. They grow in auxiliary clusters and start appearing in the beginning of spring season.

1.2 *Tribulus tarestris*: Family-Zygophyllaceae

It is a flowering plant and is native to warm temperate and tropical regions of the Old World in southern Europe, southern Asia, throughout Africa, and in northern Australia. It can thrive even in desert climates and poor soil. Like many weedy species, this plant has many common names. Puncture Vine, Caltrop, Yellow Vine, and Goathead are the most widely used. It is a taprooted herbaceous perennial plant that grows as a summer annual in colder climates. The stems radiate from the crown to a diameter of about 10 cm to over 1 m, often branching. They are usually prostrate, forming flat patches, though they may grow more upwards in shade or among taller plants. The leaves are pinnately compound with leaflets less than a quarter-inch long. The flowers are 4-10 mm wide, with five lemon-yellow petals. A week after each flower blooms, it is followed by a fruit that easily falls apart into four or five single-seeded nutlets. The nutlets or "seeds" are hard and bear two to three sharp spines, 10 mm long and 4-6 mm broad point-to-point. These nutlets strikingly resemble goats' or bulls' heads; the "horns" are sharp enough to puncture bicycle tires and to cause painful injury to bare feet.

1.3 *Tinospora cordifolia*: Family-Meninspermaceae

It is a large, climbing shrub and grows to 1.0 meters (3.3 feet) high by 0.5 meters (1.65 feet) wide and prefers many types of soil ranging from acid to alkaline and partial to full sun with moderate moisture. This plant has hermaphrodite flowers.

1.4 *Embelia basaal* Family-Myrsinaceae

*E. Basaal*, an Indian variety, with larger elliptical leaves, more or less downy, is useful in various ways. The young leaves, in combination with ginger, are used as a gargle for sore throats; the dried bark of the root as a remedy for toothache, and the ground berries, mixed with butter or lard, made into an ointment and laid on the forehead for pleuritis.

1.5 *Cyprus rotundus* (Mustaka) Family-Cyperaceae

Mustaka was held in high esteem by the ancient sage's of India. This super bulb has been used throughout the ages for the treatment of numerous illnesses. It enjoys an important place among medicinal herbs in India since ancient times. Vagbhata has admired it as the drug of choice for any type of fever. He has also mentioned it as dipaniya—an appetizer, pacaniya—digestant and sangrahi—anti—diarrhoeal. Maharishi Charaka has categorized it as trptighna—anti-saturative, trsna nigra—haniya—thirst relieving, lekhaniya—reducing herb, kandughna—anti-pruritic and stany sodhana—lactodepurant herb. It is also well known for its amapacaka—digests ama and svedala—diaphoretic properties. The plant grows all over India upto 2000 meters altitude, especially on the banks of streams and rivers. A perennial herb grows 0.33-1 meter tall, branches long and with three edges,. The spikiets in compound umbels are 5-20 cm long. The rhizomes are blackish, hard, fragrant tubers and aerial stems triquetrous. The fruits are small, ovoid and the seeds tiny, numerous.

1.6 *Picrorhiza kurroa* Family-Scrophulariaceae

*Picrorhiza kurroa* also known as kutki is found in the North-Western Himalayan region from Kashmir to Kumaun and Garhwal regions in India and Nepal. It is a small perennial herb from the Scrophulariaceae family. The rhizome of *Picrorhiza* has been traditionally used to treat worms, constipation, low fever, scorpion sting, asthma and ailments affecting the liver. Current research on *Picrorhiza kurroa* has focused on its hepatoprotective, anticholestatic, antioxidant, and immune-modulating activity.

1.7 *Withania somnifera*: Family-Solanaceae

It is an erect, evergreen, grayish tomentose shrub 0.3-2 m tall, with fairly long, stout, fleshy, whitish-brown roots. Leaves simple, alternate or subopposite, broadly ovate, glabrous, 5-12 cm long and 2.5 -7 cm wide, apex subacute, base un equal, marginsentire, finely stellate-pubescent beneath; main nerves about 6 pairs; petioles 0.3-1.7 cm long. The roots are considered alternative, germicidal, aphrodisiac and diuretic; they are used in Ayurveda to treat ulcers, fever, dyspnoea, cough, consumption, dropsy, rheumatism, toxicosis and memory loss. The powdered roots mixed with equal parts of honey and ghee is thought to be beneficial for impotence or seminal debility. The roots as well as the bruised leaves are also used externally to treat ulcers, painful swellings and scabies. The total alkaloids present in the roots produce relaxant and anti spasmodic effects. The fruits and seeds are diuretic. The leaves are considered anthelmintic and bitter, and their infusion is given to relieve fever.

1.8 *Asparagus racemosus*: Family-Liliaceae

It is a tall climbing, much-branched, spiny shrub with annual woody, white-grey or brown stems armed with strong, straight or recurved spines 0.5-1.3 cm long; rootstock short, tuberous, bearing numerous fusiform, succulent tuberous roots 30-100 cm long and 1-2 cm thick. Flowers white, fragrant, small, crowded in simple and branched racemes 5-15 cm long. Fruits globose, red when ripe, 3-lobed, 0.4 -0.6 cm in diameter.

1.9 *Pueraria tuberose*: Family-Fabaceae

It is a coarse, high-climbing, twining, trailing and perennial vine. The huge root, which can grow to the size of a human body, is the source of medicinal preparations used in traditional Chinese medicine and modem herbal products. Habitat is dry deciduous to moist deciduous forests.

1.10 *Ipomoea digitata*:Family-Convolvulaceae

The genus occurs throughout the tropical and subtropical regions of the world, and comprises annual and perennial herbaceous plants, lianas, shrubs and small trees; most of the species are twining climbing plants.

1.11 *Lepidium sativum*:Family-Brassicaceae

It is a fast-growing, edible plant botanically related to watercress and mustard and sharing their peppery, tangy flavor and aroma. In some regions, garden cress is known as garden pepper cress, pepper grass or pepperwort. Garden cress is a green perennial plant used as a leaf vegetable consumed by humans typically as a garnish. Undisturbed garden cress can grow to a height of two feet with minimal maintenance. When mature, garden cress produces white flowers, and small seedpods. Garden cress is used as a medicine in India in the system of ayurveda to prevent postnatal complications. Cress may be given to pet birds such as budgerigars for a healthy and fresh treat.

TABLE 1

Details of the medicinal herbs used in herbal calf starter compositions are as below:

| S. No | Latin Binomial | Common Names | Geographical Distribution | Parts Used | Quantity | Adverse Effects |
|---|---|---|---|---|---|---|
| 1 | *Emblica officinalis* | Amala | Throughout India | Fruit | 10-30% Preferably 20% | None |
| 2 | *Tinospora cordifolia* | Gulvel | Throughout India | Stem | 15-40% Preferably 25% | None |
| 3 | *Embelia basaal* | Vavding | Throughout India | Seeds | 5-20% Preferably 10% | None |
| 4 | *Cyprus rotundus* | Nagarmotha | Throughout India | Roots | 5-25% Preferably 15% | None |
| 5 | *Asparagus racemosus* | Shatawari | Throughout India | Roots or Leaves | 10-30% Preferably 20% | None |
| 6 | *Lepidium sativam* | Vardhara | Throughout India | Seeds | 5-20% Preferably 10% | None |
| 7 | *Tribulus terrestris* | Gokhru | Throughout India | Fruit | 10-30% Preferably 10% | None |
| 8 | *Picrorhiza kurroa* | Kutki | North-Western Himalayan region, India and Nepal | Roots | 10-25% Preferably 15% | None |
| 9 | *Withania somnifera* | Ashwagandha | Throughout India | Roots or Leaves | 20-40% Preferably 25% | None |
| 10 | *Pueraria tuberosa* | Bhuikovala | Throughout India | Roots | 10-25% Preferably 15% | None |
| 11 | *Ipomoea digitata* | Vidarikand | Throughout India | Roots | 5-20% Preferably 10% | None |

2. Energy Source: The energy source is selected from maize grind, wheat bran fine, bypass fat and ground nut extract. The energy source is added in the range of 20-50% (w/w) maize grind preferably 30% (w/w), 10-30% (w/w) wheat bran fine preferably 15% (w/w), 1-2% (w/w) bypass fat preferably 1.5% (w/w) and 2-8% (w/w) ground nut extract preferably 5% (w/w).

3. Protein Source: The protein source is selected from soya flour and maize gluten. The protein source is added in the range of 10-30% (w/w) soya flour preferably 20% (w/w) and 3-6% (w/w) maize gluten preferably 5.8% (w/w).

4. Carbohydrate source: The Carbohydrate source used to prepare the herbal calf starter composition is deoiled rice bran (DORB) and which is added in the range of 10-40% (w/w) of total composition preferably 20% (w/w).

5. Chelated/organic Mineral Mixture: The chelated/organic mineral mixture which mainly consists of the following:

| Chelated Mineral | % by weight |
|---|---|
| Zinc | 5 to 10 |
| Manganese | 1 to 4 |
| Copper | 0.5 to 2 |
| Cobalt | 0.05 to 0.25 |
| Selenium | 0.01 to 0.1 |
| Chromium | 0.05 to 0.2 |
| Iodine | 0.01 to 0.1 |

-continued

| Chelated Mineral | % by weight |
|---|---|
| Methomin | 5 to 60 |
| Tricalcium phosphate | 30 to 35 |

Preparation of Chelated/organic Mineral Mixture:

The chelated/organic minerals preferably menthomins chelated are prepared by mixing 8% (w/w) zinc, 2% (w/w) manganese, 1.2% (w/w) copper, 0.12% (w/w) cobalt, 0.05% (w/w) selenium, 0.09% (w/w) chromium, 0.04% (w/w) iodine, methomin and tricalcium phosphate. The chelated mineral mixture is added to the herbal composition in a proportion of 2% (w/w) of total composition.

6. Salt: The salt used to prepare the composition is sodium chloride and which is added in a proportion of 1% (w/w) of total composition.

7. Vitamins:

Mixture # 1: The vitamins are mixed in the following proportion-

| Vitamin | Nutritional value per gram |
|---|---|
| Vitamin A | 80,000-85,000 IU |
| Vitamin $D_3$ | 10,000-15,000 IU |
| Vitamin K | 8-12 mg |
| Vitamin $B_2$ | 40-60 mg |
| Vitamin $B_{12}$ | 12-18 mcg |

Mixture # 2: The vitamins are mixed in the following proportion-

| Vitamin | Nutritional value per gram |
|---|---|
| Vitamin $B_1$ | 7-9 mg |
| Vitamin $B_2$ | 3-5 mg |
| Vitamin $B_6$ | 14-18 mg |
| Vitamin $B_{12}$ | 70-90 mcg |
| Niacin | 110-130 mg |
| Folic Acid | 3.0-4.0 mg |
| Vitamin E | 75-85 mg |

The vitamin mixture # 1 or # 2 may be added to the herbal composition in a proportion of 0.1% (w/w) of total composition.

8. Toxin Destroyer: The toxin destroyer used in the composition is BioFix in a proportion of 0.1% (w/w) of total composition.

9. Biocide: The biocide used in the composition is Hygisoft Spray in a proportion of 0.03% (w/w) of total composition.

The composition of an effective amount of mixture of herbs and one or more additives selected from Energy Source, Protein Source, Carbohydrate source, Chelated/organic Mineral Mixture, Vitamins, Salt, Toxin destroyer and Biocide to obtain the herbal calf starter composition. The herbal mixture contains an extract and/or at least one bioactive fraction from medicinal herbs such as *Emblica officinalis, Tinospora cordifolia, Embelia basaal,Cyprus rotundus, Asparagus racemosus*, and *Lepidium sativam*. The energy source is selected from maize grind, wheat bran fine, bypass fat and ground nut extract. The protein source is selected from soya flour and maize gluten. The Carbohydrate source is deoiled rice bran (DORB). By properly adjusting a particular component in the composition to make bioavailability of essential nutrients in the intestine of calf for absorption, which enhances the overall health of calf. The synergistic formulation nourishes the calf and which results into achieving the early conception. The compositions can be used in several forms: powdered feed form, concentrate form, blender form and base mix form.

Process for Preparation of herbal calf starter composition:

Method-I

The present invention herbal calf starter compositions are prepared by one type of method comprising the following steps:

a) Obtaining the part of medicinal herb from a group comprising leaves, bark, root and aerial parts;
b) drying the plant part of step (a);
c) powdering the dried plant material of step (b) to a coarse powder;
d) extracting the powdered dried plant material at a temperature in the range of 30 to 85° C.;
e) extracting the plant material with water or alcohol or mixture of both for a period ranges from 6 hours to 6 days;
f) concentrating the obtained extract under reduced pressure at a temperature in the range of 40 to 85° C.;
g) the concentrated extract is subjected to removal of solvent;
h) mixing the effective amount by weight of above concentrated extract of medicinal herb selected from the group of *Emblica offlcinalis, Tinospora cordifolia, Embelia basaal, Cyprus rotundus, Asparagus racemosus* and *Lepidium sativam* to obtain the herbal mixture;
i) the above herbal mixture is added with one or more of the ingredients selected from Energy Source such as maize grind, wheat bran fine, bypass fat and ground nut extract; Protein Source such as soya flour and maize gluten; Carbohydrate source such as DORB, Chelated/organic Mineral Mixture, Vitamins, Salt, Toxin destroyer and Biocide to obtain the herbal calf starter composition.

Method-II

The present invention herbal calf starter compositions are prepared by another type of method comprising the steps as below:

a) Obtaining the part of medicinal herb from a group comprising leaves, bark, root and aerial parts;
b) drying the plant part of step (a);
c) powdering the dried plant material of step (b) to a coarse powder;
d) the dried and powdered plant material obtained in step (c) can be used directly to prepare the feed compositions by mixing the effective amount by weight of medicinal herb selected from the group of *Emblica Tinospora cordifolia, Embelia basaal, Cyprus rotundus, Asparagus racemosus* and *Lepidium sativam* to obtain the herbal mixture;
e) the above herbal mixture is added with one or more of the ingredients selected from Energy Source such as maize grind, wheat bran fine, bypass fat and ground nut extract; Protein Source such as soya flour and maize gluten; Carbohydrate source such as DORB, Chelated/organic Mineral Mixture, Vitamins, Salt, Toxin destroyer and Biocide to obtain the herbal calf starter composition.

EXAMPLES

The following specific examples presented to illustrate the herbal calf starter compositions which are prepared by above said method I or II but do not limit the scope of the invention and additional compositions are being prepared and tested.

TABLE 2

Specific herbal mixtures prepared are as following:

| | % by weight | | | | |
|---|---|---|---|---|---|
| Medicinal Herb | I | II | III | IV | V |
| *Emblica officinalis* | 20 | 25 | 15 | 10 | 25 |
| *Tinospora cordifolia* | 25 | 20 | 25 | 25 | 20 |
| *Embelia basaal* | 10 | 15 | 15 | 15 | 15 |
| *Cyprus rotundus* | 15 | 10 | 10 | 15 | 15 |
| *Asparagus racemosus* | 20 | 15 | 15 | 15 | 10 |
| *Lepidium sativam* | 10 | 15 | 20 | 20 | 15 |

TABLE 3

Specific herbal calf starter compositions prepared are as following:

| Ingredient | Composition (% by weight) I | II | III | IV | V |
|---|---|---|---|---|---|
| Herbal Mixture | 3 | 2 | 5 | 7 | 8 |
| Energy Source | 48.5 | 40 | 45 | 55 | 65 |
| Protein Source | 25 | 35 | 30 | 20 | 15 |
| Carbohydrate Source | 20 | 19.7 | 17.5 | 14.7 | 10 |
| Chelated/organic Mineral Mixture | 2 | 2 | 2 | 2 | 2 |
| Salt | 1 | 1 | 1 | 1 | — |
| Vitamins | 0.1 | 0.1 | 0.1 | 0.1 | — |
| Toxin Destroyer | 0.1 | 0.1 | 0.1 | 0.1 | — |
| Biocide | 0.03 | 0.03 | 0.03 | 0.03 | — |

The trials were carried out on 100 Cross-breed/indigenous cow calves and which are divided into two groups of Control group and Treatment group. The control group calves were fed with conventional calf starter. The Treatment group calves were fed from 90 days to 365 days with herbal calf starter composition (I) in a dose of 120 g/day. The conception rate in Treatment group was found to significantly higher as compared to Control group. The results of trials are depicted in Table 4.

TABLE 4

The percentage of Conception rate in cow heifer

| | Control Group | | | Treatment group | | |
|---|---|---|---|---|---|---|
| S. No. | Age group (Months) | No. of Animals conceived | % of Conception rate in cow heifer | Age group (Months) | No. of Animals conceived | % of Conception rate in cow heifer |
| 1 | 12 | 2 | 4 | 10 | 4 | 8 |
| 2 | 13 | 3 | 6 | 12 | 5 | 10 |
| 3 | 14 | 3 | 6 | 13 | 5 | 10 |
| 4 | 15 | 4 | 8 | 14 | 7 | 14 |
| 5 | 16 | 5 | 10 | 15 | 8 | 16 |
| 6 | 17 | 7 | 14 | 16 | 10 | 20 |
| 7 | 18 | 7 | 14 | 17 | 6 | 12 |
| 8 | 20 | 8 | 16 | 18 | 4 | 8 |
| 9 | 22 | 11 | 22 | 20 | 1 | 2 |

The invention claimed is:

1. A process for preparation of herbal calf starter compositions comprising:

a. obtaining a part of medicinal herb from a group comprising leaves, bark, root and aerial parts;
b. drying the plant part of step (a);
c. powdering the dried plant material of step (b) to a coarse powder;
d. mixing the effective amount by weight of the powdered or the concentrated extract of medicinal herb to obtain an herbal mixture; and,
e. adding to the above herbal mixture one or more ingredients selected from Energy Source, Protein Source, Carbohydrate Source, Chelated/organic Mineral Mixture, Vitamins, Salt, Toxin destroyer and Biocide to obtain the herbal calf starter composition.

2. An herbal calf starter composition comprising (i) herbs *Emblica officinalis, Tinospora cordifolia, Embelia basaal, Cyprus rotundus, Asparagus racemosus* and *Lepidium sativam* and/or extracts therefrom and (ii) additives including an energy source, a protein source, a carbohydrate source, a chelated/organic mineral mixture source, a vitamin source and salt.

3. An herbal calf starter composition according to claim 2 wherein the herbs and/or extracts therefrom are provided in the following ranges: 10 to 30% (w/w) *Emblica officinalis*, 15 to 40% (w/w) *Tinospora cordifolia*, 5 to 20% (w/w) *Embelia basal*, 5 to 25% (w/w) *Cyprus rotundus*, 10 to 30% (w/w) *Asparagus racemosus*, and 5 to 20% (w/w) *Lepidium sativam.*

4. An herbal calf starter composition according to claim 2 wherein the energy source is maize grind, wheat bran fine, bypass fat and/or ground nut extract.

5. An herbal calf starter composition according to claim 2 wherein the protein source is soya flour and/or maize gluten.

6. An herbal calf starter composition according to claim 2 wherein the carbohydrate source is deoiled rice bran (DORB).

7. An herbal calf starter composition according to claim 2 wherein the chelated/organic mineral mixture source includes at least two minerals selected from zinc, manganese, copper, cobalt, selenium, chromium, iodine, methomin and tricalcium phosphate.

8. An herbal calf starter composition according to claim 2 wherein the vitamin source includes at least one vitamin selected from vitamin A, vitamin B1, vitamin B2, vitamin B6, vitamin B12, niacin, folic acid, vitamin D3, vitamin E and vitamin K.

9. An herbal calf starter composition according to claim 2 further comprising a toxin destroyer and a biocide.

10. An herbal calf starter composition comprising herbs *Asparagus racemosus, Emblica officinalis, Tinospora cordifolia, Embelia basaal* and *Cyprus rotundus* and/or extracts therefrom, and a protein source.

11. An herbal calf starter composition according to claim 10 further comprising *Lepidium sativam* and/or extracts therefrom.

12. An herbal calf starter composition according to claim 10 further comprising an energy source, a carbohydrate source, a chelated/organic mineral mixture source, and a vitamin source.

13. An herbal calf starter composition according to claim 12 further comprising salt.

14. An herbal calf starter composition according to claim 12 further comprising a toxin destroyer and a biocide.

15. An herbal calf starter composition according to claim 10 further comprising *Lepidium sativam* and/or extracts therefrom, an energy source, a carbohydrate source, a chelated/organic mineral mixture source, a vitamin source, a toxin destroyer, a biocide and salt.

16. An herbal calf starter composition according to claim 15 wherein the composition comprises 1 to 10% (w/w) herbal extract, 35 to 75% (w/w) energy source, 15 to 50% (w/w) protein source, 10 to 40% (w/w) carbohydrate source, 2% (w/w) chelated/organic mineral mixture, 1% (w/w) salt, 0.1% (w/w) vitamins, 0.1% (w/w) toxin destroyer, and 0.03% (w/w) biocide.

17. An herbal calf starter composition according to claim 16 wherein the energy source is maize grind, wheat bran fine, bypass fat and/or ground nut extract, the protein source is soya flour and/or maize gluten and the carbohydrate source is deoiled rice bran (DORB).

18. An herbal calf starter composition according to claim 16 wherein the chelated/organic mineral mixture source includes at least two minerals selected from zinc, manganese, copper, cobalt, selenium, chromium, iodine, methomin and tricalcium phosphate and the vitamin source includes at least one vitamin selected from vitamin A, vitamin B1, vitamin B2, vitamin B6, vitamin B12, niacin, folic acid, vitamin D3, vitamin E and vitamin K.

19. An herbal calf starter composition consisting of (i) herbs *Emblica officinalis, Tinospora cordifolia, Embelia basaal, Cyprus rotundus, Asparagus racemosus* and *Lepidium sativam* and/or extracts therefrom; and (ii) an energy source, a protein source, a carbohydrate source, a chelated/organic mineral mixture source, a vitamin source, salt, a toxin destroyer and a biocide.

20. An herbal calf starter composition according to claim 19 wherein each component is provided in the following ranges: 1 to 10% (w/w) herbal extract, 35 to 75% (w/w) energy source, 15 to 50% (w/w) protein source, 10 to 40% (w/w) carbohydrate source, 2% (w/w) chelated/organic mineral mixture, 1% (w/w) salt, 0.1% (w/w) vitamins, 0.1% (w/w) toxin destroyer, and 0.03% (w/w) biocide, said ranges not to exceed 100% in combination.

* * * * *